(12) United States Patent
Renard et al.

(10) Patent No.: US 9,308,231 B2
(45) Date of Patent: Apr. 12, 2016

(54) ANTI-INFLAMMATORY COMPOSITION COMPRISING MALVIDIN-3-O-β-GLUCOSIDE AND A PROPOLIS EXTRACT

(75) Inventors: Loïc Renard, Rueil Malmaison (FR); Djavad M. Mossalyai, Bordeaux (FR); Maryam Mossalyai, legal representative, Bordeaux (FR); Jean-Michel Merillon, Martillac (FR)

(73) Assignees: UNIVERSITE DE BORDEAUX, Bordeaux (FR); NUTRIVERCELL, Evry (FR)

( * ) Notice: Subject to any disclaimer, the term of this patent is extended or adjusted under 35 U.S.C. 154(b) by 108 days.

(21) Appl. No.: 14/343,449

(22) PCT Filed: Sep. 7, 2012

(86) PCT No.: PCT/EP2012/067584
§ 371 (c)(1),
(2), (4) Date: May 27, 2014

(87) PCT Pub. No.: WO2013/034746
PCT Pub. Date: Mar. 14, 2013

(65) Prior Publication Data
US 2014/0314888 A1  Oct. 23, 2014

(30) Foreign Application Priority Data
Sep. 8, 2011 (FR) .................... 11 57995

(51) Int. Cl.
| | | |
|---|---|---|
| *A01N 65/00* | (2009.01) | |
| *A61K 36/18* | (2006.01) | |
| *A23L 1/30* | (2006.01) | |
| *A23L 1/076* | (2006.01) | |
| *A61K 36/87* | (2006.01) | |
| *A61K 45/06* | (2006.01) | |
| *A61K 31/165* | (2006.01) | |
| *A61K 31/192* | (2006.01) | |
| *A61K 31/352* | (2006.01) | |
| *A61K 35/644* | (2015.01) | |
| *A61K 31/7048* | (2006.01) | |

(52) U.S. Cl.
CPC ............. *A61K 36/18* (2013.01); *A23L 1/076* (2013.01); *A23L 1/3002* (2013.01); *A61K 31/165* (2013.01); *A61K 31/192* (2013.01); *A61K 31/352* (2013.01); *A61K 31/7048* (2013.01); *A61K 35/644* (2013.01); *A61K 36/87* (2013.01); *A61K 45/06* (2013.01)

(58) Field of Classification Search
CPC ........................................... A61K 36/00
USPC .......................................... 424/725
See application file for complete search history.

(56) References Cited

FOREIGN PATENT DOCUMENTS

| | | |
|---|---|---|
| CN | 1994357 A | 7/2007 |
| FR | 2916141 A1 | 11/2008 |
| JP | 2005001998 A | 1/2005 |

OTHER PUBLICATIONS

International Search Report for PCT/EP2012/067584 Nov. 13, 2011.
Database WPI, Thompson Scientific 2005-076593.
Borrelli, F. et, al. "Phytochemical compounds involved in the anti-inflammatory effect of propolis extract" IN: FITOTERAPIA ; vol. 73, No. Supplement 1, No. 2002, pp. S53-S63.

*Primary Examiner* — Michael Meller
(74) *Attorney, Agent, or Firm* — B. Aaron Schulman, Esq.; Stites & Harbison, PLLC.

(57) ABSTRACT

The present invention relates to an anti-inflammatory composition comprising a plant extract and a propolis extract.

16 Claims, No Drawings

ANTI-INFLAMMATORY COMPOSITION COMPRISING MALVIDIN-3-O-β-GLUCOSIDE AND A PROPOLIS EXTRACT

This application is a National Stage application of PCT international application PCT/EP2012/067584, filed on Sep. 7, 2012 which claims the priority of French Patent Application No. 11 57795 entitled "ANTI-INFLAMMATORY COMPOSITION", filed with the European Patent Office on Sep. 8, 2011, both of which are incorporated herein by reference in their entirety.

The present invention relates to an anti-inflammatory composition comprising a plant extract comprising a specific content of malvidine-3-O-β-glucoside and a propolis extract. The invention more particularly relates to the use of this composition in the treatment of inflammatory diseases, notably arthritises.

Present management of inflammatory pathologies and notably of arthritis is in majority based on the use of steroidak anti-inflammatory agents (corticoids) or of non-steroidal anti-inflammatory agents such as ibuprofene, ketoprofene, niflumic acid and diclofenac.

However, there exist major drawbacks related to the use of these anti-inflammatory agents, notably their detrimental effects on the stomach (gastric or duodenal ulcers).

Moreover, there exist basic treatments which participate in the extinction of the symptoms of the inflammation, such as sulfasalazines (Salazopyrine®).

However, many drawbacks persist with these treatments, notably the long term toxicity of molecules such as corticoids but also the absence of prevention in the occurrence of the inflammation.

The anti-inflammatory activity of propolis, notably of caffeic acid or of its ester contained in propolis is known (Borelli et al., Fitoterapia (2002), 73 Suppl 1, 53-63).

However, this activity, when the propolis content is limited, is insufficient for inhibiting the inflammatory response in the case of chronic inflammatory diseases such as arthritises.

The anti-inflammatory activity of anthocyans, notably of malvidine and its glucoside, is also known (Wang et al., J. Agric. Food. Chem (2002), 50, 850-857).

Document FR 2 916 141 describes the use of malvidine-3-O-β-glucoside in a medical composition for preventing or treating a pathology involving chronic or acute inflammatory processes notably rheumatoid polyarthritis.

However, there do not exist today any atoxic compositions, notably food or topical compositions, having anti-inflammatory activity, notably against arthritises, the efficiency of which is close or even equivalent to anti-inflammatory agents commonly used.

Thus, a first object of the invention consists of proposing a composition which gets rid of the drawbacks of the state of the art and which provides a solution to all or part of the problems of the state of the art.

Another object is to propose an anti-inflammatory composition, the efficiency of which on the treatment of pathologies involving chronic or acute inflammatory processes, notably of our arthritis, is close or even equivalent to that of the presently available compositions.

Another object is to propose an atoxic anti-inflammatory composition which may appear in the form of a food or topical use composition.

Another object of the invention is to propose an anti-inflammatory composition which may be combined with other anti-inflammatory agents, such as cortisone or methotrexate, thereby decreasing the risks of toxicity related to their use.

The object of the present invention is an anti-inflammatory composition comprising:
(a) a plant extract comprising at least 5% by weight, preferably from 5 to 20% by weight, advantageously from 5 to 15% by weight of malvidine-3-O-β-glucoside; and
(b) a propolis extract comprising caffeic acid or one of its esters, ferulic acid, galangin and pinocembrin;
in a plant extract/propolis extract a/b weight ratio ranging from 1/4 to 4/1

Malvidine-3-O-β-glucoside is a glucoside derivative of malvadine having the following formula:

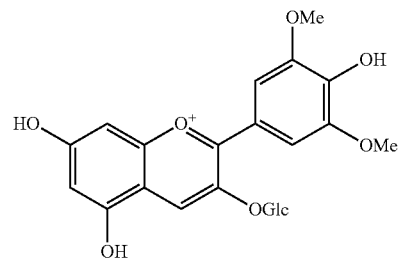

According to the invention, the plant extract may be selected from extracts of grape, blueberries (*Vaccinium* spp), blackberries (*Rubus fruticosus*) or further of red cabbages (*Brassica oleracea* var. *capitata* f. *rubra*).

According to the invention, the plant extract is advantageously selected from grape cuticle extracts.

According to the invention, the grape cuticle extract is obtained or may be obtained by a method comprising the concentration of the polyphenolic fractions of at least one red grape marc.

By grape marc, is meant the whole formed by the cuticles, the pips and stalk obtained from pressing the grapes after having separated them from the must.

According to the invention, red grape marc advantageously stems from the pressing of grape bunches from vine varieties: Merlot, Cabernets such as Sauvignon or Franc, Syrah, Gamays, Grenache, Tannat or Alicanthe Bouchet or mixtures thereof.

According to the invention, the grape cuticle extract is advantageously obtained by a method comprising the selection of at least one red grape marc and the concentration of the polyphenolic fractions of said marc.

The method for obtaining the grape cuticle extract may notably comprise a first step for selecting red grape marcs and then diffusion of said marc in the presence of an aqueous dispersion of sulfur dioxide.

It is then proceeded with centrifugation, and then with concentration of the polyphenolic fractions, notably by evaporation followed by concentration in vacuo.

The thereby obtained product may be subject to atomization thus allowing grape cuticle extract to be obtained in the form of a powder comprising at least 5% by weight of malvidine-3-O-β-glucoside, as well as low residual humidity.

The proportion of malvidine-3-O-β-glucoside of the plant extracts is notably measured by the HPLC method coupled with a UV-Visible DAD spectrophotometer (detection at 535 nm) by using a reverse phase C18 column and a solvent gradient consisting of trifluoroacetic acid and acetonitrile.

As an example of grape cuticle extract, mention may be made of an extract of grape cuticles comprising 10% by weight of malvidine-3-O-β-glucoside marketed by GRAP'SUD under the Anthos-vin reference.

The content by weight of plant extract in the composition according to the invention ranges from 0.1 to 50%, preferably from 1 to 40%.

Propolis designates a whole series of resin, gum and balsam substances of viscous consistency, collected on certain portions, notably buds and barks of plants by bees which transport them to the hive and partly modify them with addition of their own saliva secretions and wax. These plants are mainly trees such as pines, firs, spruces, poplars, alders, willows, horse chestnuts, birches, plum trees, ashes, oaks or further elms.

By propolis extract is meant a form of propolis which may be applied. It may therefore be non-transformed or untreated, or else transformed notably in the presence of a suitable excipient, for example carob, starch or starch derivative, e.g. maltodextrin. Propolis may notably appear as a powder. For this, propolis may be mixed with a hydro-alcoholic solution to which is added an excipient, such as maltodextrin or carob powder, as a carrier. The thereby obtained mixture is evaporated and then dried. A propolis extract comprising 18% of propolis and 82% of carob powder is further marketed under the name of propolis PPM 18 by LUSTREL. Another example of propolis extract comprising 60% of propolis and 40% of carob is marketed by Plantex.

The content by weight of propolis extract in the composition according to the invention ranges from 20 to 80%, preferably from 30 to 70%.

According to the invention, the propolis extract comprises a content by weight of caffeic acid or of one of its esters from 0.001 to 0.2%, preferably from 0.005 to 0.15%, of ferulic acid from 0.0001 to 0.005%, preferably from 0.0005 to 0.003%, of galangin from 0.05 to 10%, preferably from 0.1 to 6% and of pinocembrin from 0.1 to 5%, preferably from 0.2 to 3%.

Caffeic acid or (E) 3-(3,4-dihydroxyphenyl)prop-2-enoic acid is a hydroxycarboxylic acid having the following formula:

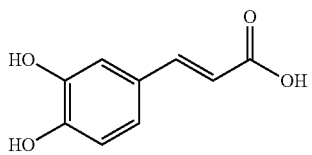 [SMILES: O=C(O)/C=C/c1ccc(O)c(O)c1]

Ferulic acid or 3-(4-hydroxy-3-methoxyphenyl)prop-2-enoic acid is a hydroxycarboxylic acid having the following formula:

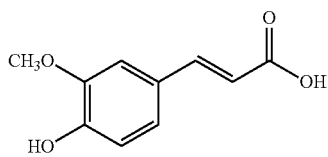

Galangin or 3,5,7-trihydroxy-2-phenylchromen-4-one is a flavonoid derivative having the following formula:

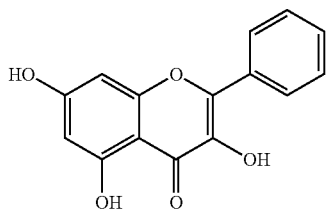 [SMILES: O=c1c(O)c(-c2ccccc2)oc2cc(O)cc(O)c12]

Pinocembrin or (2R,3R)-3,5,7-trihydroxy-2-phenyl-chroman-4-one is a flavonoid derivative having the following formula:

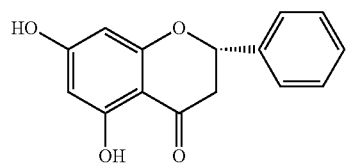 [SMILES: O=C1C[C@@H](c2ccccc2)Oc2cc(O)cc(O)c21]

Further, the composition according to the invention may also comprise at least one additional active compound which may be selected from analgesic agents, preferably capsaicin, advantageously stemming from Cayenne peppers, anti-bacterial agents, preferably a cranberry extract, advantageously an extract of *Vaccinium macrocarpon* cranberry, anti-inflammatory agents or a mixture thereof.

In an embodiment, the composition according to invention also comprises capsaicin or an anti-inflammatory agent or a mixture thereof.

The content by weight of capsaicin in the composition according to the invention ranges from 0.01 to 0.1%, preferably from 0.025 to 0.075%.

As examples of cranberry extracts, mention may be made of those described in document WO 2011/020957, and notably the one marketed by Tournay Biotechnologies under reference Exocyan CRAN 20S.

The content by weight in the composition according to the invention of cranberry extract ranges from 5 to 40%.

Further, the composition according to the invention may also comprise a food ingredient.

Advantageously, the food ingredient is piperine.

Piperine may stem from various sources such as mushrooms or black, white or grey pepper.

Advantageously, piperine stems from black, white or grey pepper, preferably black pepper. As an example, mention may be made of the dry extract of black pepper marketed by Plantex comprising from 10 to 15% of piperine.

Without being bound to any theory in particular, piperine may promote absorption as well as bioavailability of the active compounds present in the composition according to the invention, notably of malvidine-3-O-β-glucoside, caffeic acid or one of its esters, ferulic acid, galangin and/or pinocembrin, thus allowing improvement in the anti-inflammatory effectiveness of the composition according to the invention.

According to the invention, the content by weight of piperine in the composition according to the invention ranges from 0.01 to 4%, preferably from 0.1 to 1%.

The food ingredient may also be selected in the group formed by zinc and its derivatives.

According to the invention, zinc derivatives may be selected from zinc salts, such as zinc citrate, zinc oxide, zinc sulfate, zinc acetate or zinc gluconate.

Advantageously, the zinc salt is zinc sulfate.

According to the invention, the content by weight of zinc or of one of its derivatives in the composition according to the invention ranges from 0.01 to 2%, preferably from 0.1 to 1.5%.

Another aspect of the invention relates to the preparation of a composition according to the invention, comprising
(i) preparing a plant extract comprising at least 5% by weight, preferably from 5 to 20% by weight, advantageously from 5 to 15% by weight, of malvidine-3-O-β-glucoside,
(ii) mixing the extract from (i) and a propolis extract.

Advantageously, the invention relates to the preparation of a composition according to the invention, comprising:
  (i) preparing a grape cuticle extract obtained by selecting at least one red grape marc and concentrating the polyphenolic fractions of said marc, and
  (ii) mixing the extract from (i) and a propolis extract.

Advantageously, the invention relates to the preparation of a composition according to the invention, comprising:
  (i) preparing a grape cuticle extract obtained by selecting at least one red grape marc and concentrating the polyphenolic fractions of said marc, said grape cuticle extract comprising at least 5% by weight, preferably from 5 to 20% by weight, advantageously from 5 to 15% by weight, of malvidine-3-O-β-glucoside, and
  (ii) mixing the extract from (i) and a propolis extract.

The whole of the different characteristics or preferences of the composition according to the invention shown for the grape cuticle extract and the propolis extract as well as those relative to their contents also apply to the method according to the invention.

The composition according to the invention may appear in solid or liquid form.

In a particular embodiment, the invention provides a kit comprising:
  (a) a first composition comprising a plant extract,
  (b) a second composition comprising a propolis extract.

The whole of the different characteristics or preferences of the composition according to the invention shown for the plant extract (a) and the propolis extract (b) as well as those relative to their contents also apply to the kit according to the invention.

Another aspect of the present invention relates to a food supplement comprising a composition according to the invention.

In an embodiment, the food supplement gives the possibility of reducing, treating and/or preventing acute or chronic inflammatory diseases.

By acute or chronic inflammatory diseases, is meant any pathology or disorder involving acute or chronic inflammatory processes.

Many human pathologies involving inflammation are known, notably arthritis; rheumatoid polyarthritis; erythematous lupus, in particular systemic lupus; Hashimoto thyroiditis, multiple sclerosis, in particular disseminated sclerosis; diabetes, in particular self-immune diabetes; uveitis, dermatitis; psoriasis; urticarias; inflammatory nephrotic syndrome; glomerulonephritis; inflammatory colon disease; ulcerative colitis; celiac disease; Crohn's disease; Sjogren's syndrome; allergies; asthma; allergic asthma; rhinitises; eczema; endometriosis; diseases related to organ implants or reactions of the grafts against the host; chronic obstructive pulmonary diseases (COPDs); bronchitises, in particular chronic bronchitises; Parkinson's diseases; Alzheimer diseases or inflammatory skin diseases.

In a preferred embodiment, the food supplement according to the invention is intended for treating and/or preventing arthritises.

The food supplement may further comprise an excipient or an inert non-toxic carrier, for example selected from gelling agents of plant origin, preferably gelatin.

As an inert excipient, mention may be made of sugars such as lactose or fructose, cellulose, calcium carbonate, tricalcium phosphate, magnesium phosphate, calcium stearate, magnesium stearate, talcum, colloidal amorphous silica.

The food supplement may also comprise a compound selected from the group formed by polyols such as glycerin or sorbitol; coloring agents; sweeteners such as sucralose or aromatic actives such as ethyl vanillin or menthol.

The food supplement according to the invention may appear as a powder, gelatin capsules, capsules, chewing gums, granules, granulates, cachets, pills, lozenges, caplets or tablets. Galenic application is carried out under conditions of temperatures and pressure which observe the integrity of the supplied ingredients and the bioactivity of the active ingredients.

In the case when the composition according to the invention appears as a food supplement, a daily effective dose is administered, called a recommended daily allowance (RDA), of the composition according to the invention. By RDA, is meant a dose of the composition according to the invention consumed over a period of 24 hours.

By RDA, is notably meant an amount of composition according to invention which comprises between 100 and 400 mg of plant extract and between 250 and 1,000 mg of propolis extract.

The dosage for administering the food supplement, for example as gelatin capsules, may vary from 2 to 8 gelatin capsules per day, depending on the nature and on the seriousness of the inflammation, to be renewed if need be.

Another aspect of the present invention relates to a composition for topical use comprising a composition according to the invention for treating and/or preventing acute or chronic inflammatory diseases, in particular intended for treating and/or preventing arthritises.

The composition for topical use may appear in the form of an emulsion of water-in-oil, oil-in-water, water-in-oil in water, oil-in-water in oil or an anhydrous formulation. The composition may appear in galenic form for external use like a cream, an ointment or a gel.

According to the invention, the composition's topical use is applied by spreading it on the skin region(s) exhibiting inflammation.

Another aspect of the present invention also relates to a drug comprising a composition according to the invention for treating and/or preventing acute or chronic inflammatory diseases, in particular intended for treating and/or preventing arthritises.

Another aspect of the present invention further relates to treatment methods comprising administration via an oral route or topical application in a mammal, notably a human, of a composition according to invention for treating and/or preventing acute or chronic inflammatory diseases, the composition according to the invention may for example appear as a food supplement, a composition for topical use or a drug as defined earlier.

In a preferred embodiment, the treatment method comprises administration via an oral route or topical application of a composition according to the invention for treating and/or preventing arthritises.

This treatment may be associated with an anti-inflammatory therapeutic treatment, notably with the administration of an anti-inflammatory agent, notably selected from steroidal or non-steroidal anti-inflammatory agents The object of the invention is therefore also the use of the composition according to the invention for proceeding, completing and/or following a therapeutic or preventive anti-inflammatory treatment. This means that the practitioner prescribes to the patient who is in need thereof, to consume the food supplement or the drug or apply the composition for topical use according to the invention in a course of treatment before, during and/or after conducting a treatment with an anti-inflammatory agent.

Another aspect of the present invention relates to a kit comprising:
- a first composition comprising a plant extract (a) and a propolis extract (b),
- a second composition comprising an anti-inflammatory agent.

The whole of the different features or preferences of the composition according to the invention shown for the plant extract (a) and the propolis extraction (b) as well as those relative to their contents and their ratio also apply to the kit according to the invention.

The anti-inflammatory agents used in the kit according to the invention may be selected from steroidal or non-steroidal anti-inflammatory agents.

The various aspects of the invention will be better understood upon reading the examples which follow. These examples are given as an indication, without any limitation.

EXAMPLE 1

Production of a Grape Cuticle Extract

After having selected a red grape marc from grapes of Merlot, Cabernets and Syrah vines, it is proceeded with diffusion in the presence of an aqueous dispersion of sulfur dioxide.

Centrifugation with gravity comprised between 7,000 and 7,500 G and a dwelling time ranging from 10 to 20 s is then applied to the thereby obtained product.

At the end of this centrifugation, the polyphenols are concentrated in the product by evaporation, the thereby obtained product being characterized by a dry material content ranging from 30 to 35%.

It is then proceeded with concentration in vacuo depressurized to 50 mbars absolute, the thereby obtained concentrate being characterized by a dry material content greater than or equal to 35%.

The thereby obtained concentrate is then dehydrated by atomization; the concentrate is thus sprayed in hot air, slightly depressurized.

The thereby obtained product appears as a powder characterized by a content of malvidine-3-O-β-glucoside equal to 10% by weight and with a relative humidity of less than 10%.

EXAMPLE 2

Production of Propolis Extract

After having harvested crude propolis, the latter is put into a hydro-alcoholic solution, is filtered, concentrated in vacuo and then pasteurized. It is then mixed with carob powder as a carrier and a drying step by atomization (stray drying) is then applied to the mixture, said mixture is then sifted. The thereby obtained propolis extract appears as a powder which contains 60% of active propolis.

The propolis extract is characterized by an average content by weight of caffeic acid equal to 0.05%, of ferulic acid equal to 0.001%, of galangin equal 1.6% and of pinocembrin equal to 1%.

EXAMPLE 3

Food Supplement in the Form of a Gelatin Capsule Comprising a Composition According to the Invention

| | |
|---|---|
| Grape cuticle extract [1] | 0.100 g |
| Propolis extract [2] | 0.200 g |

[1] Anthos-Vin marketed by Grap'Sud
[2] propolis marketed by Plantex

The composition according to Example 3 appears as a powder and is conditioned in a gelatin capsule and the dosage of use is from 2 to 4 gelatin capsules daily, to be renewed if need be.

EXAMPLES 4 AND 5

Food Supplements in the Form of a Gelatin Capsule Comprising a Composition According to the Invention

| | Example 4 | Example 5 |
|---|---|---|
| Grape cuticle extract [1] | 0.1 g | 0.05 g |
| Propolis extract [2] | 0.25 g | 0.125 g |
| Plant gelatin | 0.094 g | 0.094 g |
| Magnesium stearate | 0.01 g | 0.01 g |
| Menthol at 1/11 | 0.01 g | 0.01 g |
| Ethyl vanillin | 0.01 g | 0.01 g |
| Precipitated amorphous silica | 3.81 g | 3.81 g |

[1] Anthos-vin marketed by Grap'Sud
[2] propolis marketed by Plantex

The composition according to Example 4 appears as a powder and is conditioned in gelatin capsules.

The dosage of use is from 2 to 6 gelatin capsules per day, to be renewed if need be.

The composition according to Example 5 appears as a powder and is conditioned in gelatin capsules.

The dosage in a flash treatment is of 4 gelatin capsules every 12 hours for the first 48 hours, and then two gelatin capsules every 12 hours for the next 48 hours, and if need be, from 1 to 2 gelatin capsules every 12 hours during the next 48 hours.

The dosage in a preventive treatment is from 1 to 2 gelatin capsules to be renewed if need be.

EXAMPLES 6, 7 AND 8

Food Supplements in the Form of a Gelatin Capsule Comprising a Composition According to the Invention

| | Example 6 | Example 7 | Example 8 |
|---|---|---|---|
| Grape cuticle extract [1] | 0.125 g | 0.125 g | 0.125 g |
| Propolis extract [2] | 0.150 g | 0.150 g | 0.150 g |
| Black pepper extract [3] | 0.020 g | | |
| Zinc sulfate | 0.006 g | | 0.006 g |
| Excipients | QSP | QSP | QSP |

[1] Anthos-vin marketed by Grap'Sud
[2] propolis marketed by Plantex
[3] Black pepper extract with 10% piperine marketed by Plantex The compositions according to Examples 6, 7 and 8 appear as a powder and are conditions in gelatin capsules.

Their dosage of use in a prevented treatment is 2 gelatin capsules daily for 30 days, to be renewed if need be.

Their dosage of use in a flash treatment is 2 gelatin capsules every 12 hours for 5 days.

EXAMPLE 9

Topical Composition as a Gel Comprising a Composition According to the Invention

| | |
|---|---|
| Hydro-alcoholic solution of a grape cuticle extract[1] | 5-10% |
| Hydro-alcoholic solution of a propolis extract[2] | 2-4% |
| Hydrating agents | 0.1-10% |
| Gelling agents | 0.5-20% |
| Purified water + preservatives | qsp |

[1] Anthos-vin marketed by Grap'Sud
[2] propolis marketed by Plantex

The composition is prepared by mixing hydro-alcoholic solutions of grape cuticle extract and propolis extract, and then adding gelling and hydrating agents and finally the balance with water and preservatives, in order to obtain the desired texture.

The application dosage is from 1 to 4 applications daily, to be renewed if need be.

EXAMPLE 10

Study of the Hematotoxicity of Grape Cuticle, Propolis Extracts as Well as of a Cranberry Extract as an Additional Active Compound The object of this study is to show that the various extracts which may be incorporated into a composition according to the invention, has no toxic action on human cells.

Cell cultures and dosages of cytokines were carried out.
The three evaluated extracts are the following:
Grape cuticle extract (Anthos-vin), re-suspended to 331 mg/ml in 100% ethanol,
propolis extract, be suspended to 500 mg/ml in 70% ethanol,
Cranberry extract, re-suspended to 50 mg/ml in 90% methanol.

Human mononuclear cells were isolated from peripheral blood of 3 different healthy donors. The technique used was isolation on a Ficoll gradient. Between Ficoll and plasma, a cell ring is established, consisting of monocytes and lymphocytes. The latter is recovered and washed in PBS (Phosphate Buffered Saline) for counting on a Malassez Cell.

The blood mononuclear cells (PBMC, Peripheral Blood Mononuclear Cells) are cultivated ($10^6$/ml) in an amount of $10^5$ cells per well in a 96-well plate for hematoxicity tests, in an RPMI (Roswell Park Memorial Institute) medium supplemented with 10% of decomplemented fetal calf serum FCS, and antibiotics, in order to avoid a bacterial infection: penicillin (100 UI/ml) and streptavidin (100 μg/ml).

The cell proliferation test with MTS (3-(4,5-dimethylthiazol-2-yl)-5-(3-carboxymethoxyphenyl)-2-(4-sulfophenyl)-2H-tetrazolium) is a colorimetric method for determining the number of viable proliferating cells. The test uses the transformation of MTS into formazan (colored product) which is soluble in the cell culture medium. The absorbance of formazan may be directly read at 490 nm with a spectrophotometer. Reduction of MTS into soluble formazan is induced by dehydrogenases involved in the metabolism of the activated cells.

The PBMCs are cultivated in an amount of $10^5$ per well of 96-well plates in a quiescent condition (naive cells) or in a proliferative condition (in the presence of Bacto-Phytohemagglutinin P (PHA, Difco) at 0.5 μg/ml). PHA has a mitotic activity on T lymphocytes and induces their proliferation.

The extracts were tested on PBMCs from 2 different donors, in quadruplicate, at different concentrations: 8, 17, 33 and 66 μg/ml for Anthos-vin; and 5, 20, 50 and 100 μg/ml for the propolis and cranberry, comparatively to PBMCs on which no extract was tested.

None of the 3 extracts exhibited any cytotoxicity on the hematopoietic cells of two donors in a culture, although they were tested at concentrations ranging up to 200 μg/ml for the propolis and cranberry extracts, and 66 μg/ml for the grape cuticle extract.

No toxicity was observed in the compositions associating grape cuticle extract and propolis extract, or in those associating grape cuticle extract, propolis extract and cranberry extract.

EXAMPLE 11

Study of the in Vitro Anti-inflammatory Activity of a Composition According to the Invention This study has the goal of demonstrating the in vitro anti-inflammatory activity of compositions according to the invention, a first composition associating grape cuticle extract (Anthos-vin) and propolis extract and a second associating grape cuticle extract (Anthos-vin), propolis extract and cranberry extract.

Cell cultures and dosages of cytokines were carried out.
The following compositions were tested:
Compositions according to the invention:
a composition comprising 8 μg/ml of Anthos-vin and 25 μg/ml of propolis extract,
a composition comprising 16 μg/ml of Anthos-vin and 50 μg/ml of propolis extract,
a composition comprising 33 μg/ml of Anthos-vin and 100 μg/ml of propolis extract,
a composition comprising 8 μg/ml of Anthos-vin, 25 μg/ml of propolis extract and 25 μg/ml of cranberry extract,
a composition comprising 16 μg/ml of Anthos-vin, 50 μg/ml of propolis extract and 50 μg/ml of cranberry extract,
a composition comprising 33 μg/ml of Anthos-vin, 100 μg/ml of propolis extract and 100 μg/ml of cranberry extract.
Reference Compositions
a composition comprising 8 μg/ml of Anthos-vin,
a composition comprising 16 μg/ml of Anthos-vin,
a composition comprising 33 μg/ml of Anthos-vin,
a composition comprising 25 μg/ml of propolis extract,
a composition comprising 50 μg/ml of propolis extract,
a composition comprising 100 μg/ml of propolis extract,
a composition comprising 25 μg/ml of cranberry extract,
a composition comprising 50 μg/ml of cranberry extract,
a composition comprising 100 μg/ml of cranberry extract.

The PBMCs were isolated from peripheral blood of 3 different healthy donors. The technique used was isolation on a Ficoll gradient. Between Ficoll and plasma, a cell ring is established consisting of monocytes and lymphocytes. The latter is recovered and washed on PBS for counting on a Malassez Cell.

Rat macrophages were isolated by washing with PBS the peritoneum of the animals, by centrifugation of the latter and washing in PBS for counting on a Malassez Cell.

The PBMCs were cultivated ($10^6$/ml) in and around of $5.10^5$ cells per well in a 24-well plate, in RPMI medium supplemented with 10% of decomplimented FCS and antibiotics: penicillin (100 IU/ml) and streptavidin (100 μg/ml).

The rat macrophages were cultivated ($10^6$/ml) in an amount of $5.10^5$ cells per well in a 24-well plate, in RPMI medium supplemented with 10% of decomplemented FCS and antibiotics: penicillin (100 IU/ml) and streptavidin (100 μg/ml).

In order to induce an inflammatory reaction on the PMBCs and the rat macrophages, the cells are incubated in the presence of LPS (bacterial LipoPolySaccharide, a pro-inflammatory product) at 10 μg/ml for 48 h.

Dosage of NO: after 48 h of cultivation of rat peritoneal macrophages, the supernatants were sampled. NO has high chemical reactivity. In the presence of water, this free radical is rapidly oxidized in a stoichiometric way and thus forms nitrite ions ($NO_2^-$) according to the reaction:

$$4NO^0 + O_2 + H_2O \rightarrow 4NO_2^- + 4H^+$$

The nitrites accumulate in the media and are easily chemically detectable by the Griess method (Kolb et al., 1994):

Griess A: 1% sulfanilamide in HCl 1.2N,
Griess B: 0.3% naphthylene diamine dihydrochloride in distilled water To 60 μl of Griess A and 60 μl of Griess B, 50 μl of culture supernatant to be assayed were added. The calorimetric reaction developed away from light for 10 mins. The optical densities obtained at 540 nm were corrected by subtraction of the ODs obtained on wells containing the culture medium alone.

Assay of the mediators of the inflammation: 48 hours after activation by LPS of the PBMCs, 25 μl of cell supernatant were sampled and immediately tested for assaying pro- and anti-inflammatory cytokines by the FlowCytomix technique.

Human FlowCytomix is an immunoassay system with fluorescent beads for quantitative detection by flow cytometry of Interferon-γ, Interleukin-1β, Interleukin-2, Interleukin-4, Interleukin-5, Interleukin-6, Interleukin-8, Interleukin-10, Interleukin-12p70 and the Tumor Necrosis Factor α and β in the culture supernatants.

Microspheres were coated with antibodies specially directed against each cytokine detected by the multiplex system. The beads may be differentiated by their size and by their spectral emission. A mixture of each coated bead for each cytokine was incubated with the sample or the standard range. The cytokines present in the sample bind to the antibody attached to the fluorescent bead. A second antibody coupled with biotin was added to the mixture, this specific antibody binds to the cytokines captured by the first antibody.

Streptavidin-phycoerythrin was added, it binds to the biotin conjugate and emits a fluorescent signal.

Assay of Prostaglandin $E_2$: the transduction routes of the signal of the eicosanoids are extremely preserved and involved in many physiopathological processes. Prostaglandins are synthesized from arachidonic acid by cyclooxygenases (COX-1 and COX-2), which convert the acid into prostaglandin $H_2$ ($PGH_2$). The latter is then transformed by microsomal or cytosolic prostaglandin synthases into prostaglandins $E_2$ ($PGE_2$) or in various other prostanoids.

$PGE_2$ is produced by a wide variety of tissues and in many physiopathological conditions, including inflammations, arthritises, fever, lesioned tissues, endometriosis and many cancers.

$PGE_2$ was assayed in the culture supernatants by means of an ELISA assay kit (Tebu-Bio, Le Perray en Yvelines, France).

Forty-eight hours after activation by LPS of the PBMCs, 100 μl of cell supernatant are sampled and immediately tested for assaying $PGE_2$.

Table 1 shows the obtained results and shows the effects of the various compositions on the level of pro-inflammatory mediators.

TABLE 1

| Compounds | μg/ml | TNF-α* | IL-1β | IL-6 | PGE2 | IL-10 | IL-8 | IFN-γ | NO |
|---|---|---|---|---|---|---|---|---|---|
| Anthos-vin | 8 | 72 | 70 | 67 | — | 0 | 51 | 0 | 0 |
|  | 16 | 66 | 70 | 67 | — | 5 | 66 | 0 | 0 |
|  | 33 | 63 | 72 | 69 | — | 41 | 69 | 39 | 0 |
| Propolis extract | 25 | 16 | 32 | 27 | — | 50 | 3 | 100 | 15 |
|  | 50 | 55 | 52 | 55 | — | 100 | 2 | 100 | 55 |
|  | 100 | 97 | 87 | 92 | — | 100 | 27 | 94 | 90 |
| Cranberry extract | 25 | 15 | 5 | 7 | — | 0 | 6 | 5 | 0 |
|  | 50 | 20 | 4 | 0 | — | 0 | 6 | 0 | 0 |
|  | 100 | 31 | 9 | 0 | — | 0 | 11 | 16 | 0 |
| Anthos-vin + propolis extract | 8 + 25 | 0 | 75 | 34 | 40 | 71 | 11 | — | — |
|  | 16 + 50 | 50 | 92 | 82 | 64 | 94 | 0 | — | — |
|  | 33 + 100 | 73 | 98 | 98 | 94 | 100 | 39 | — | — |
| Anthos-vin + propolis extract + cranberry extract | 8 + 25 + 25 | 0 | 76 | 72 | 61 | 98 | 0 | 94 | — |
|  | 16 + 50 + 50 | 100 | 99 | 97 | 76 | 100 | 0 | 100 | — |
|  | 33 + 100 + 100 | 95 | 99 | 99 | 82 | 100 | 41 | 89 | — |

*Percentage of inhibition as compared with activated cells in the absence of the extracts These results show that the composition according to the invention associating Anthos-vin and propolis have a better global anti-inflammatory action than those comprising Anthos-vin or propolis alone.

These results also show that the composition according to the invention associating Anthos-vin, propolis and cranberry has a significant action against TNF-α and IFN-γ, while cranberry alone is only of little interest for anti-inflammatory action.

In order to confirm these results, a composition according to the invention was tested, comprising (33 μg of Anthos-vin+ 100 μg of propolis extract)/ml, on the transcription of genes coding for inflammatory molecules in humans.

The cell cultures and the assays of cytokines were carried out.

Human mononuclear cells were isolated from peripheral blood of a donor. The technique used was isolation on a Ficoll gradient. Between Ficoll and plasma, a cell ring was established consisting of monocytes and of lymphocytes. The latter was recovered and washed in PBS for counting on a Malassez Cell.

The PBMCs were cultivated ($10^6$/ml) in an amount of $1.10^7$ cells per well in a 6-well plate, in RPMI medium supplemented with 10% of decomplemented FCS and antibiotics: penicillin (100 IU/ml) and streptavidin (100 µg/ml).

An inflammatory reaction was induced on the PBMCs. Rapidly the cells were incubated in the presence of LPS.

Quantitative PCR gives the possibility of profiling 84 key genes.

At an inflammatory level, real-time PCR allows measurement of the genic expression of 84 genes representing the main pro-/anti-inflammatory mediators (chemokines, receptors for chemokines, cytokines, receptors for cytokines and genes related to the inflammatory pattern) but also those involved in the transduction of the signal, apoptosis and the cell cycle. By using real-time PCR, it is possible to analyze the expression of a targeted panel of genes relatively to the inflammatory reaction.

The targeted genes are listed below:
Molecules of the transduction groups: FOS, HSF1, HSP90AA2, HSP90AB1, HSPB1, JUN, IKBKB, MYC, NFKB1, NOX5, STAT1, STAT3, TANK;
Molecules involved in the apoptotic routes: BAD, BAX, BCL2, CASP10, CASP3, CASP9, TP53;
Adhesion molecules: ICAM1, ITGAX, SELE, SELPLG, VCAM1;
Molecules of the cell cycle: CCNC, CCND1, CDKN1B, CDKN2B, MAP2K1, MAPK1, MAPK11;
Chemokines and Cytokines: CCL3 (MIP-1a), CCL20 (MIP-3a), CXCL9, CXCL10 (IP-10), CXCL11 (I-TAC/IP-9), IFNA2, IFR1, IL10, IL17C, IL1A, IL1B, IL2, IL22, IL4, IL6, IL8, LTA, LTB, MIF, TGFB2, TGFB3;
Receptors of Cytokines: IL1RN;
Ligands of TNF and receptors: CD40LG, FAS, FASLG, LTA (LT-a), LTB (LT-b), TNF (TNF-a), TNFRSF1A (TNFR1), TNFRSF10A TNFRSF10B.
Other factors involved in the inflammatory response: C3, CAT, CRP, CYP1A1, CYP2E1, CYP7A1, GPX1, ICEBERG, MMP1, MMP10, MMP3, MMP7, NOS, NOS2A, NOS3, PRKCA, SOD1, SOD2.

The total RNA of the cells was extracted by means of an extraction kit (Qiagen, France). This RNA was analyzed qualitatively and quantitatively in order to check the whole of this material. An RNA sample was put in a 1% agarose gel at 80V for migration in order to verify the presence of ribosomal 28S and 16S RNAs, of transfer RNA and of messenger RNAs (qualitative measurement).

Further, this RNA was assayed at 230 nm, 260 nm and 280 nm in order to be quantified and to check for the absence of protein contaminants.

1 µg of RNA was used for real-time PCR. By means of a kit (eBioscience, France), the RNA was back-transcribed into cDNA and then amplified by PCR.

Simultaneously with the amplification, the use of a fluorescent probe (Sybergreen) allowed real-time measurement of the integration of the genome bases. The whole of the results was analyzed by means of a suitable software package Moreover, the use of a real-time PCR apparatus is required (Stratagene MX3000P).

Table 2 below shows the main significant modifications of the transcription of the pro-inflammatory genes in cells incubated with the composition according to the invention as compared with untreated cells.

TABLE 2

| Genes | Names | Up-regulated | Down-regulated |
|---|---|---|---|
| IL1B | (Interleukin 1, beta) | | −116.81 |
| IL1A | (Interleukin 1, alpha) | | −57.20 |
| C3 | (Complement component 3) | | −45.82 |
| IL6 | (Interleukin 6 (interferon, beta 2)) | | −40.73 |
| CCL3 | (Chemokine (C-C unit) ligand 3) | | −21.53 |
| IL1RN | (Interleukin 1 receptor antagonist) | | −18.74 |
| IL8 | (Interleukin 8) | | −5.23 |
| TGFB2 | (Transforming growth factor, beta 2) | +17.78 | |
| HSP90AA2 | (Heat shock protein 90 kDa alpha (cytosolic), class A member 2) | +12.75 | |
| HSPB1 | (Heat shock 27 kDa protein 1) | +11.41 | |
| HSP90AB1 | (Heat shock protein 90 kDa alpha (cytosolic), class B member 1) | +8.77 | |
| TNF | (Tumor necrosis factor (TNF superfamily, member2)) | +8.47 | |
| BAX | (BCL-2 associated X protein) | +6.24 | |
| IFNA2 | (Interferon, alpha 2) | +5.99 | |
| SOD1 | (Superoxide dismutase 1, soluble (amyotrophic lateral sclerosis 1 (adult)) | +5.00 | |
| BCL2 | (B-cell CLL/lymphoma 2) | +3.19 | |
| IL2 | (Interleukin 2) | +3.49 | |

The results show that the genes in connection with the inflammation are in majority inhibited (IL-1, C3, IL-6 and IL-8).

Further, in the presence of a composition according to the invention, transcription of TGFβ2 and of interferon-α, which are both well-known molecules for anti-inflammatory action, is increased.

Moreover, the results also show that the RNAs coding for the protective proteins of the cells (HSP, DAX, BCL-2, SOD1) are increased which confirms the absence of toxicity of the composition according to the invention on human cells.

EXAMPLE 12

Study of the in vivo Anti-inflammatory Activity of a Composition According to the Invention This study was carried out with the goal of confirming the results of the study in vitro. For this, various compositions according to the invention were tested in vivo in the arthritic rat model. This model consists of developing a chronic inflammation attack in young rats by injecting a bacterial antigen. This model has the advantage of having many similarities with symptoms of rheumatoid polyarthritis in humans: symmetry in the involved joints, peripheral joints which are preferentially affected, synovial hyperplasia, infiltration of inflammatory cells, marginal erosions and better susceptibility of the disease in females. Unlike human rheumatoid polyarthritis, no trace amounts of rheumatoid factors are detected in the serum.

It should be noted that the inflammatory condition of the rats is very advanced (as compared with humans) and requires therapeutic doses which are 10-20 times greater than those used in humans (test carried out with corticotherapy), in particular via the oral route.

Female Lewis rats of six weeks of age were immunized by intradermal injection at the base of the tail, of 60 mg of *Mycobacterium butyricum* killed by heat and emulsified in an oily solution.

At J+7, a second immunization, under the same conditions, was carried out. The first clinical signs appear at J+14.

The rats rapidly develop arthritis at the peripheral joints (essentially the hind legs) with a strong inflammatory reaction of the synovial cavity expressed by quasi paralysis of the relevant joint and destructive erosion of the bone tissue. Like in many pathological models, the animal is subject to a strong weight loss.

The inflammatory symptoms are evaluated according to a pre-established clinical score and summarized in Table 3:

TABLE 3

| Clinical score | Symptoms |
| --- | --- |
| Score 0 | No leg inflammation |
| Score 1 | Inflammation/paralysis of a leg |
| Score 2 | Inflammation/paralysis of two legs |
| Score 3 | Inflammation/paralysis of three legs |
| Score 4 | Inflammation/paralysis of four legs |

For seven days before the 1$^{st}$ immunization with *Mycobacterium butyricum*, the rats are separated into several groups:
Group 1: negative controls, healthy rats;
Group 2: positive controls, rats having experimental arthritis without any treatment;
Group 3: arthritic rats receiving 5 doses (one every two days) of a composition according to the invention comprising 30 mg of Anthos-vin and 100 mg of propolis extract per kg of animal and per dose, from the 1$^{st}$ day of occurrence of the symptoms;
Group 4: arthritic rats continually receiving every 2 days, a dose of a composition according to the invention comprising 30 mg of Anthos-vin and 100 mg of propolis extract per kg of animal and per dose, from the 1$^{st}$ day of the symptoms and until the end of the study (J+50);
Group 5: arthritic rats receiving 5 doses (one every 2 days) of a composition of according to the invention comprising 150 mg of Anthos-vin and 500 mg of propolis extract per kg of animal and per dose, from the 1$^{st}$ day of occurrence of the symptoms;
Group 6: arthritic rats continually receiving every 2 days, a dose of a composition according to the invention comprising 150 mg of Anthos-vin and 500 mg of propolis extract per kg of animal and per dose from the 1$^{st}$ day of the symptoms and until the end of the study (J+50).

From the occurrence of the symptoms, the rats of Groups 3, 4, 5 and 6 receive orally (force-feeding) every 2 days their treatment, i.e. for 10 days (Groups 3 and 5) or continually (Groups 4 and 6).

They are weighed daily and their clinical score is noted.
The results of the study are shown in Tables 4 and 5.

TABLE 4

| Group of rats | Average cumulative score |
| --- | --- |
| Group 2 | 82 |
| Group 3 | 39 |
| Group 4 | 6 |
| Group 5 | 62 |
| Group 6 | 37 |

The whole of the rats treated with one of the compositions according to the invention have much smaller clinical scores as compared with untreated rats.

The compositions according to the invention strongly reduce the severity of the pathological signs. The number of affected legs and inflammation of the latter are considerably reduced.

It should be noted that the rats receiving moderate doses continuously (Groups 4 and 6) exhibit better response as compared with the other rats receiving 5 doses (Groups 3 and 5).

Moreover, no apparent toxicity was observed in rats of the Groups 3, 4, 5 and 6 (and no bleeding, nausea, diarrhea, loss of appetite).

TABLE 5

| Group(s) of rats | Cumulative score (after 50 days) |
| --- | --- |
| Group 2 | 327 |
| Group 3 + Group 4 | 111 |
| Group 5 + Group 6 | 208 |

These results confirm that the tested compositions according to the invention give the possibility of very significantly reducing the importance of the pathological signs.

The invention claimed is:

1. An anti-inflammatory composition in a form selected from the group consisting of gelatin capsules, capsules, chewing gums, pills, lozenges, caplets and tablets, said composition consisting essentially of therapeutically effective amounts of propolis extract and grape cuticle extract.

2. The composition of claim 1 wherein the grape cuticle extract consists essentially of at least 5% by weight of malvidine-3-O-β-glucoside.

3. The composition of claim 1 wherein the propolis extract consists essentially of caffeic acid or one of its esters, ferulic acid, galangin and pinocembrin.

4. The composition of claim 1 wherein the weight ratio of grape cuticle extract to propolis extract ranges from 1/4 to 4/1.

5. The composition of claim 1 wherein:
from 0.1 to 50% by weight of the grape cuticle extract, and
from 20 to 80% by weight of propolis extract is in the composition.

6. The composition according to claim 1, wherein the propolis extract contains
from 0.001 to 0.2% by weight of caffeic acid or of one of its esters;
from 0.0001 to 0.005% by weight of ferulic acid;
from between 0.05 to 10% by weight of galangin; and
from 0.1 to 5% by weight of pinocembrin.

7. The composition according to claim 1, wherein the propolis extract is in the form of a powder.

8. The composition according to claim 1, wherein the propolis extract is in the form of a powder mixed with an excipient.

9. The composition according to claim 8, wherein the excipient is carob or starch.

10. The composition according to claim 8, wherein the excipient is maltodextrin or carob powder.

11. The composition according to claim 1, which also consists essentially of capsaicin or an anti-inflammatory agent or a mixture thereof.

12. The composition according to claim 11, wherein said composition contains from 0.01 to 0.1% by weight of capsaicin.

13. The composition according to claim 1, wherein the composition also contains piperine or zinc.

14. The composition according to claim 13, wherein the piperine is present at a concentration from 0.01 to 4% by weight.

15. The composition according to claim 13, wherein the zinc is present at a concentration from 0.01 to 2% by weight of zinc.

16. A kit consisting essentially of:
a first composition according to claim 1, and
a second composition of an anti-inflammatory agent.

* * * * *